United States Patent [19]
Zilberman et al.

[11] Patent Number: 5,824,022
[45] Date of Patent: Oct. 20, 1998

[54] COCHLEAR STIMULATION SYSTEM EMPLOYING BEHIND-THE-EAR SPEECH PROCESSOR WITH REMOTE CONTROL

[75] Inventors: Yitzhak Zilberman, St. Louis, France; Steven A. Hazard, Palmdale, Calif.

[73] Assignee: Advanced Bionics Corporation, Sylmar, Calif.

[21] Appl. No.: 807,534

[22] Filed: Feb. 28, 1997

Related U.S. Application Data

[60] Provisional application No. 60/012,971 Mar. 7, 1996.
[51] Int. Cl. [6] ............................... A61N 1/36; H04R 25/00
[52] U.S. Cl. ............................................... 607/57; 128/903
[58] Field of Search ....................... 607/55–57; 128/903

[56] References Cited

U.S. PATENT DOCUMENTS

| | | | |
|---|---|---|---|
| 5,095,904 | 3/1992 | Seligman et al. | 607/57 |
| 5,514,175 | 5/1996 | Kim et al. | |
| 5,531,774 | 7/1996 | Schulman et al. | 607/57 |
| 5,569,307 | 10/1996 | Schulman et al. | |
| 5,601,617 | 2/1997 | Loeb et al. | 607/56 |
| 5,626,629 | 5/1997 | Faltys et al. | |

*Primary Examiner*—William E. Kamm
*Assistant Examiner*—Carl H. Layno
*Attorney, Agent, or Firm*—Bryant R. Gold

[57] ABSTRACT

A cochlear stimulation system includes (1) an implantable cochlear stimulator (ICS); (2) a behind-the-ear (BTE) wearable speech processor, including: coils for inductively coupling with the ICS, a first microphone, an LED indicator, and an FM receiver; (3) a remote control unit (RCU), including an FM transmitter, mode/control switches, a second microphone, an input jack for interfacing with external audio equipment, and a status indicator; and (4) an external programmer, including one or more ports for coupling the external programmer with a personal computer. The external programmer is used to program the ICS through the BTE processor to operate in a desired manner, and to perform tests on the ICS. Once the ICS is initially programmed, the user controls the sounds he or she "hears" with the ICS through the RCU, which RCU (when turned ON) is electronically coupled to the BTE processor through an FM (or other wireless) link. Through the RCU, the user may control, e.g., the operating mode, volume, sensitivity, and microphone location of the BTE speech processor. With the RCU microphone turned ON, the RCU may be given to, or placed near, a teacher, performer or other person located remotely from the ICS user, thereby allowing the user to "hear" such remote person (through the FM link) just as though the person were standing next to the user. Other electronic devices, e.g., tape or CD players, may similarly be coupled directly to the user by connecting their audio outputs to the input jack of the RCU.

21 Claims, 4 Drawing Sheets

COCHLEAR STIMULATION SYSTEM EMPLOYING BEHIND-THE-EAR SPEECH PROCESSOR WITH REMOTE CONTROL

This application claims priority to U.S. Provisional Application Serial No. 60/012,971, filed Mar. 7, 1996.

FIELD OF THE INVENTION

The present invention relates to hearing prostheses for aiding the profoundly deaf, and more particularly to cochlear stimulation systems which directly stimulate the auditory nerve with electrical impulses as a function of externally perceived sound waves.

BACKGROUND OF THE INVENTION

Cochlear stimulation systems are known in the art. Such systems are used to help the profoundly deaf (those whose middle and/or outer ear is dysfunctional, but whose auditory nerve remains intact) to hear. The sensation of hearing is achieved by directly exciting the auditory nerve with controlled impulses of electrical current, which impulses are generated as a function of perceived audio sounds. The audio sounds are picked up by a microphone carried externally (not implanted) by the deaf person and converted to electrical signals. The electrical signals, in turn, are processed and conditioned by an external speech processor in an appropriate manner, e.g., converted to a sequence of pulses of varying width and/or amplitude, and then transmitted to an implanted receiver circuit. The implanted receiver circuit is connected to an implanted electrode array that has been inserted into the cochlea of the inner ear. Electrical current is applied to individual electrode pairs of the electrode array by the implanted receiver circuit as a function of the processed signal it receives from the external speech processor (which in turn is based on the audio sounds picked up the external microphone). It is this electrical current which directly stimulates the auditory nerve and provides the user with the sensation of hearing.

A representation of a typical cochlear stimulation system as is known in the art is illustrated in FIG. 1. The system includes an external speech processor 12 connected to a headpiece 14 via a cable 16. A microphone 18 is typically mounted to, or made an integral part of, the headpiece 14. Audio sounds sensed by the microphone 18 are converted to corresponding audio signals which are sent to the speech processor 12 over dedicated wires in cable 16 to be processed by the speech processor 12. The speech processor 12 processes the received audio signals in accordance with a selected speech processing strategy. The processed signals are then sent back to the headpiece 14 over the same or additional wires in the cable 16. Included in the headpiece 14 is one or more coils (not shown) which receive the processed signals from the speech processor 12 and inductively couple these signals to corresponding coils in an implanted receiver 20. The implanted receiver 20 is also called an implanted cochlear stimulator (ICS). The ICS 20 is integrally connected to a cochlear electrode array 22, which is inserted into the snail-shaped cochlea of the inner ear of the user using known surgical techniques and tools. The electrode array 22 includes a plurality of individual electrodes 24 which are paired in an appropriate manner for electrical stimulation of the cochlea.

A magnet in the headpiece 14 aligns the headpiece with a corresponding magnet in the ICS 20 as known in the art. Such magnet also holds the headpiece in place on the head of the user. For some users, the headpiece 14 is easily hidden under a nice crop of hair or attractive clothing or head gear. For other users, however, the headpiece cannot be easily hidden, leaving such users very conscious and ill-at-ease in wearing the headpiece. A way is needed, therefore, that allows all users to easily and comfortably wear the headpiece without being self-conscious of its presence.

The speech processor 12 is typically worn or carried by the user on a belt or pocket, and is thus sometimes referred to as a "wearable processor". While the processor 12 is not too large, it is likewise not extremely small, and hence also represents an inconvenience for the user. The cable 16, which must connect the processor 12 with the headpiece 14, is particularly a source of irritation and self-consciousness for the user. What is needed, therefore, is an external speech processor and corresponding headpiece that is small, unobtrusive, lightweight, and which eliminates the need for the troublesome interconnecting cable 16 between the speech processor and the headpiece.

SUMMARY OF THE INVENTION

The present invention addresses the above and other needs by providing a cochlear stimulation system that includes: (1) a multichannel implantable cochlear stimulator (ICS); (2) a behind-the-ear (BTE) wearable speech processor, including: coils for inductively coupling with the ICS, a first microphone, an LED indicator, and an FM receiver; (3) a remote control unit (RCU), including: an FM transmitter, mode/control switches, a second microphone, an input jack for interfacing with external audio equipment, and a status indicator; and (4) an external programmer, including an FM transmitter and one or more ports for coupling with a personal computer.

The external programmer is used to program the ICS through the BTE processor to operate in a desired manner, and to perform tests on the ICS. Once the ICS is initially programmed, the user controls the sounds he or she "hears" with the ICS through the RCU, which RCU (when turned ON) is electronically coupled to the BTE processor through an FM link. Through the RCU, the user may control, e.g., the operating mode, volume, sensitivity, and microphone location of the BTE speech processor. With the RCU microphone turned ON, the RCU may be given to, or placed near, a teacher, performer or other person located remotely from the ICS user, thereby allowing the user to "hear" such remote person (through the FM link) just as though the person were standing next to the user. Other electronic devices, e.g., tape or CD players, radios, or televisions, may similarly be coupled through the FM link to the user by connecting their audio outputs to the input jack of the RCU.

The LED indicator on the BTE processor is activated to indicate a successful link between the ICS and the BTE speech processor. However, because such ICS/BTE-speech-processor link is also activated through the RCU, activation of the LED also provides a visual verification of a working FM link between the RCU and the BTE processor. Thus, e.g., a teacher who has a student wearing a BTE processor in his or her classroom may place the RCU of that student on his or her desk (or carry the RCU on his or her person), and then may selectively activate the BTE speech processor of that student, causing the LED to light, thereby allowing the teacher to visually verify that the RCU signals are being received by the BTE processor worn by the student, and that a successful link has been established between the BTE processor and the ICS. Once the presence of the correct link is verified, the teacher can then activate the RCU microphone, which is near the teacher. Any audio sounds originating near the teacher (i.e., words spoken by the teacher) are then readily picked up by the RCU microphone, converted to an FM signal, forwarded to the FM receiver in the BTE speech processor, appropriately processed, and coupled to the ICS for direct stimulation of the cochlea. In this way, the student is able to readily hear what the teacher is saying, even though the student may be some distance from the teacher.

In accordance with one aspect of the invention, the audio signals sensed by the two microphones used with the system—one microphone being in or near the BTE processor, and the other microphone being part of or coupled to the RCU—are appropriately combined before being coupled into the ICS. For example, when the RCU microphone is turned ON, or when another audio source (e.g., tape player) is connected to the RCU, the level of the signal from the BTE microphone is significantly reduced so that the audio signal received from the RCU over the FM link predominates what the ICS user hears. However, as soon as the signal received from the RCU over the FM link fades away, i.e., when the audio source at the remote site ceases to provide an audio signal input, then the signal level from the BTE microphone returns to a normal level, so that the audio sounds sensed by the BTE microphone predominate what the ICS user hears. These adjustments between the BTE microphone and the RCU microphone (or other audio source) may be done dynamically so that the appropriate audio signals heard by the ICS user fade in and fade out as a function of whether one signal exceeds a prescribed threshold level. Thus, for example, so long as a signal coming by way of the RCU microphone is above a certain level, it masks out any signal from the BTE microphone. But, as soon as the RCU microphone signal drops below that certain level, then the BTE microphone signal is no longer masked out. Alternatively, for some applications, an appropriate command generated from the RCU may turn the BTE microphone completely OFF and the RCU microphone ON all the time, or the BTE microphone ON all the time and the RCU microphone OFF all the time, so that audio signals from only one audio-pickup point are received by the ICS.

In accordance with another aspect of the invention, one RCU operating in an FM transmit mode, i.e., with the RCU microphone turned on, may be shared between several ICS users. For example, in a classroom there may be several students having an ICS, each wearing their own BTE processor, with each student also having an individual RCU. All of the RCU's, except one, are placed in a mode wherein the RCU microphone is turned off or inactive. One of the RCU's is given to the teacher, with the RCU microphone being turned on. This RCU with the activated microphone is placed on the teacher's desk (or carried by the teacher) and thus broadcasts sounds sensed by the activated RCU microphone to all the ICS users over the same FM channel. This allows all the ICS users to listen to the same speaker without competing signals from their own RCU.

It is thus an object of the present invention to provide a cochlear stimulation system that does away with the need for an external headpiece separate and apart from an externally-worn speech processor, thereby eliminating the unsightly and bothersome cable that has heretofore been required for interconnecting the headpiece and speech processor.

It is a further object of the invention to provide such a cochlear stimulation system wherein the external speech processor and headpiece comprise one integral unit that is worn comfortably and unobtrusively behind the ear, much like a conventional hearing aid is worn.

It is a feature of the invention to provide such a cochlear stimulation system wherein the behind-the-ear (BTE) speech processor/headpiece is controlled, at least in part, by a remote control unit (RCU) carried by the user that is telecommunicatively coupled—e.g., through a radio frequency (e.g., FM), ultra-sonic, infrared, or other wireless link, to the BTE speech processor.

It is yet an additional feature of the invention to provide an FM receiver in the BTE speech processor and an FM transmitter in the RCU that allows an FM link to be established and tested between the BTE processor and RCU, over which FM link command signals can be sent from the RCU to the BTE processor.

If is still a further feature of the invention to provide such an FM-linked BTE speech processor and RCU wherein audio signals originating at the RCU, whether from a microphone or an auxiliary audio source (such as a tape-player or radio) can be sent to the BTE processor over the FM link.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
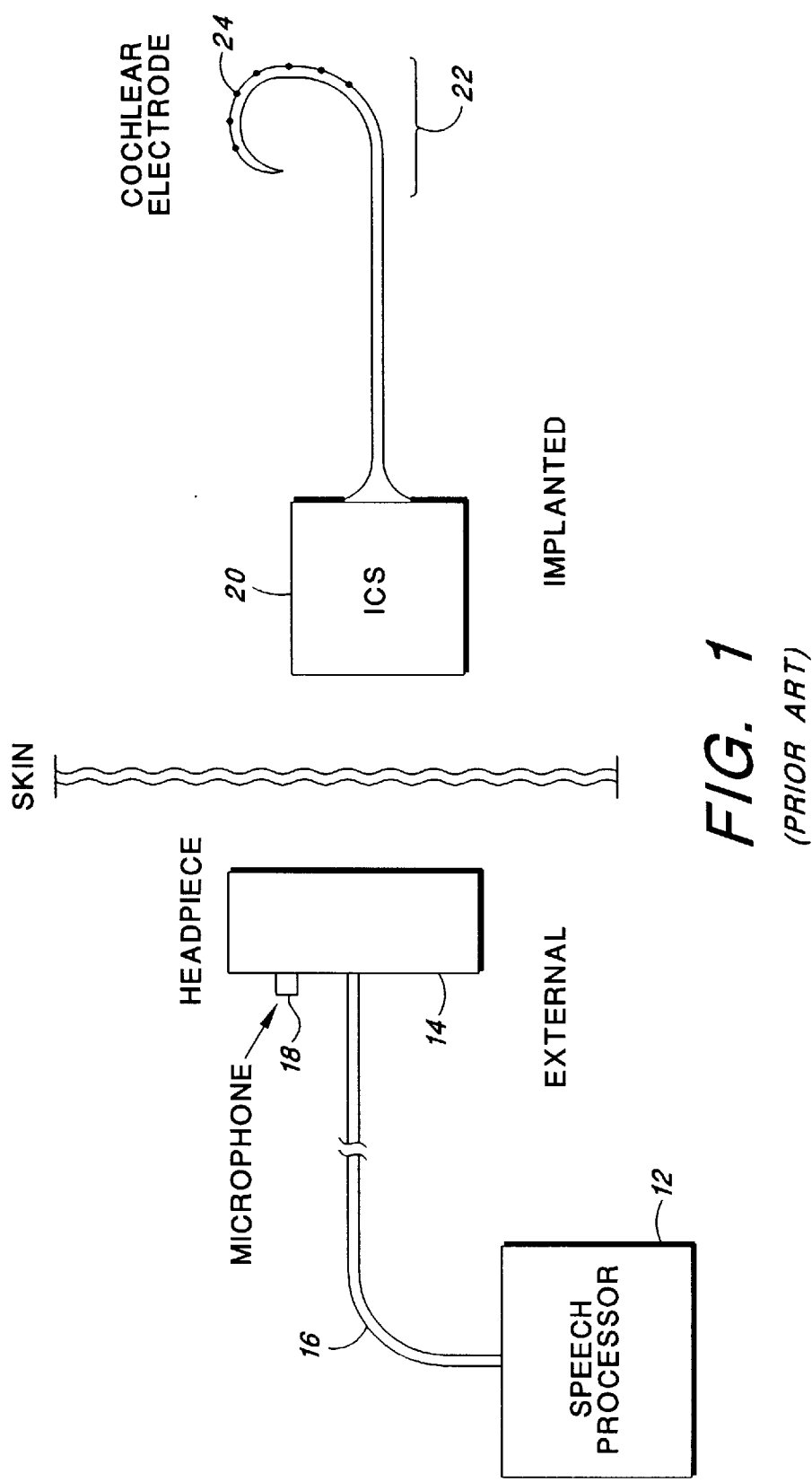
FIG. 1 is block diagram of a prior art cochlear stimulation system, including an ICS with implanted electrode array, an externally-worn headpiece, and an externally-worn speech processor that is connected to the headpiece via a cable.

An explanation of the prior art system of FIG. 1 was presented above in the "Background" portion of this application, and will not be repeated here. Suffice it to say that any cochlear stimulation system typically includes an implanted portion and a non-implanted (external) portion, and that the implantable cochlear stimulator and electrode array that comprise the implantable portion of the present invention may be substantially the same as the ICS 20 and electrode array 22 shown in FIG. 1, or used with any other system. That is, the present invention may be used with any suitable ICS and electrode array, now known or yet to be developed. The inventive aspects of the present invention do not relate to the implantable portions of the system. A suitable ICS and electrode array that may be used with the invention are disclosed, e.g., in U.S. Pat. Nos. 4,819,647; 4,837,049; 4,991,582; and 5,569,307, all of which patents are incorporated herein by reference.

Figure 2:
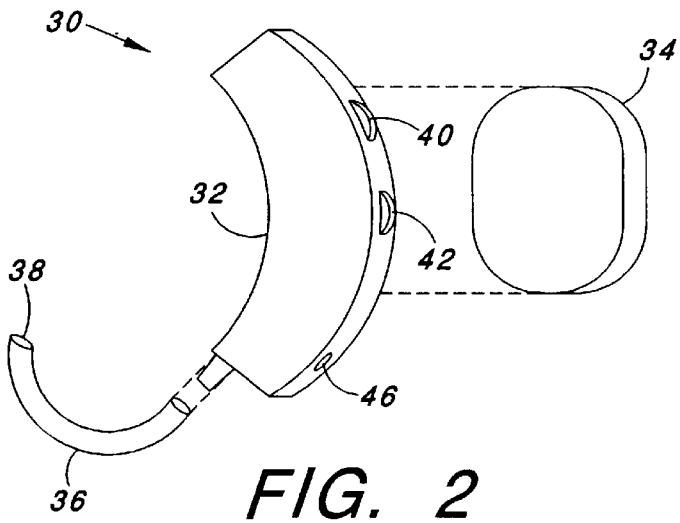
FIG. 2 is an exploded view of a behind-the-ear (BTE) speech processor/headpiece made in accordance with the present invention.
Figures 3A, 3B:
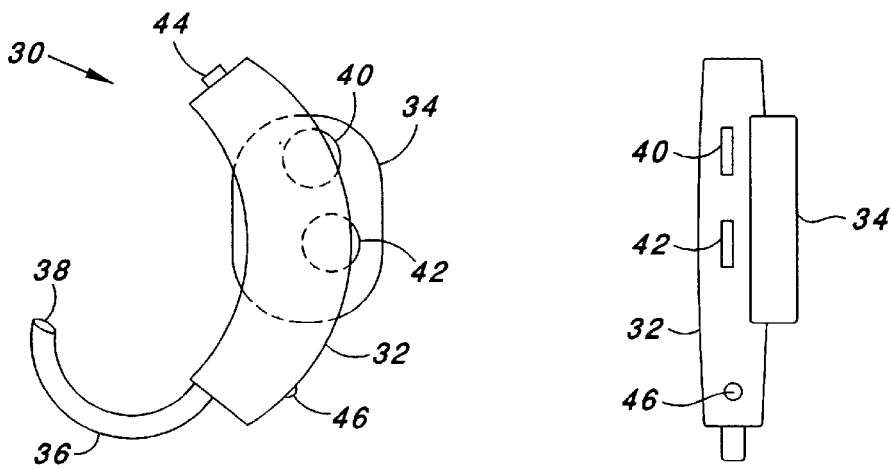
FIG. 3A shows a side view of the BTE speech processor/headpiece of FIG. 2.
FIG. 3B shows an end view of the BTE speech processor/headpiece of FIG. 2.

FIGS. 2, 3A and 3B show, respectively, an exploded view, a side view, and an end view, of a behind-the-ear (BTE) speech processor/headpiece 30 made in accordance with one embodiment of the present invention. For the embodiment shown in these figures, the BTE processor 30 includes a case 32 formed and shaped to fit behind the ear of a user, much like a conventional hearing aid. Many, if not all, of the electronic circuits used by the processor 30 are housed within the case 32. Some of the electronics, including the coils used to inductively couple the BTE processor 30 with an ICS (not shown) may be housed in a headpiece assembly 34, which is affixed to the case 32. As desired, or required, a microphone tube 36 is also coupled to the one end of the case 32, allowing a microphone 38 to be positioned inside of, or near, the ear canal (which is where audio sounds are normally directed and detected). Alternatively, and/or conjunctively, a microphone may be embedded within the case 32.

User-accessible controls on the case 32 include a volume control knob 40, a sensitivity control knob 42, and an ON/OFF button switch 44. An LED 46 is also mounted at a location on the case 32 where it can be seen by someone looking for it.

The BTE processor 30 is typically worn behind the ear of its user, in an unobtrusive manner, and has the appearance of a conventional hearing aid.

Figure 4:
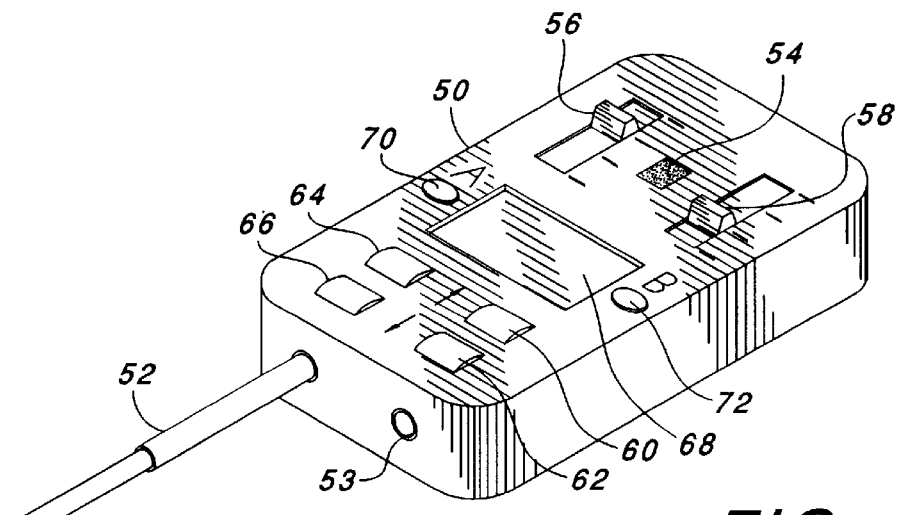
FIG. 4 is a perspective view of one embodiment of a remote control unit (RCU) that may be used to control the BTE speech processor/headpiece of FIG. 2.

Turning next to FIG. 4, a perspective view of one embodiment of a remote control unit (RCU) 50 that may be used to control the BTE speech processor 30 is depicted. The RCU 50 is preferably a relatively small unit, e.g., no larger than the size of a package of cigarettes (and preferably somewhat smaller), thereby allowing the RCU to be easily and unobtrusively carried by the user in a pocket of clothing or in a purse, yet large enough to allow the RCU to be easily located should it be set down on a table or counter top or elsewhere. The case of the RCU is made from a ruggedized plastic, or other light, strong material, which protects the circuitry housed therein from being damaged should the RCU be dropped or stepped on. In another embodiment (not shown in FIG. 4), the RCU 50 may take the form of a conventional wrist watch that is worn on the user's wrist.

A antenna 52 extends from one end of the RCU 59. This antenna may be a telescoping antenna, as shown in FIG. 4, or simply a wire antenna. An audio input plug 53 permits audio signals from an auxiliary source, e.g., a CD player, tape player, radio or television, to be inputted directly into the circuits of the RCU 50. A microphone 54 is embedded into the case of the RCU 50. A first mode switch 56 (shown as a sliding switch in FIG. 4, but which could be any type of switch) sets the mode of the RCU to a desired operating mode. Exemplary operating modes of the RCU include: (1) RCU OFF, (2) RCU ON as FM transmitter, (3) RCU ON as a remote control; and (4) RCU ON as an FM transmitter with microphone OFF. A second mode switch 58 controls the mode for the BTE processor 30. Such BTE processor modes may include, for example: (1) BTE Processor OFF, (2) BTE ON with Speech Processing Strategy A; (3) BTE ON with Speech Processing Strategy B; and (4) BTE ON with Speech Processing Strategy C. The speech processing strategies A, B and C, may comprise any suitable speech processing strategies now known, or yet developed, that facilitate the conversion of sensed audio sounds to electrical stimuli that can be perceived by the user as sounds, i.e., that can be "heard". For example, Speech Processing Strategy A could be a Continuous Analog (CA) strategy, Speech Processing Strategy B could be an ascending Continuous Interleaved Sampling (CIS) strategy, and Speech Processing Strategy C could be a non-sequential CIS strategy.

Still with reference to FIG. 4, additional controls included on the RCU 50 include UP and DOWN volume control buttons 60 and 62, and UP and DOWN sensitivity control buttons 64 and 66. A display panel 68, e.g., made from a LCD display of the same type (although with different display capabilities) as is used in a conventional wristwatch, is also included as part of the RCU 50, as are "A" and "B" programming buttons. Other controls may also be included within the capability of the RCU 50, as needed, and/or desired. For example, a BTE LED activate button may be included.

Figure 6:
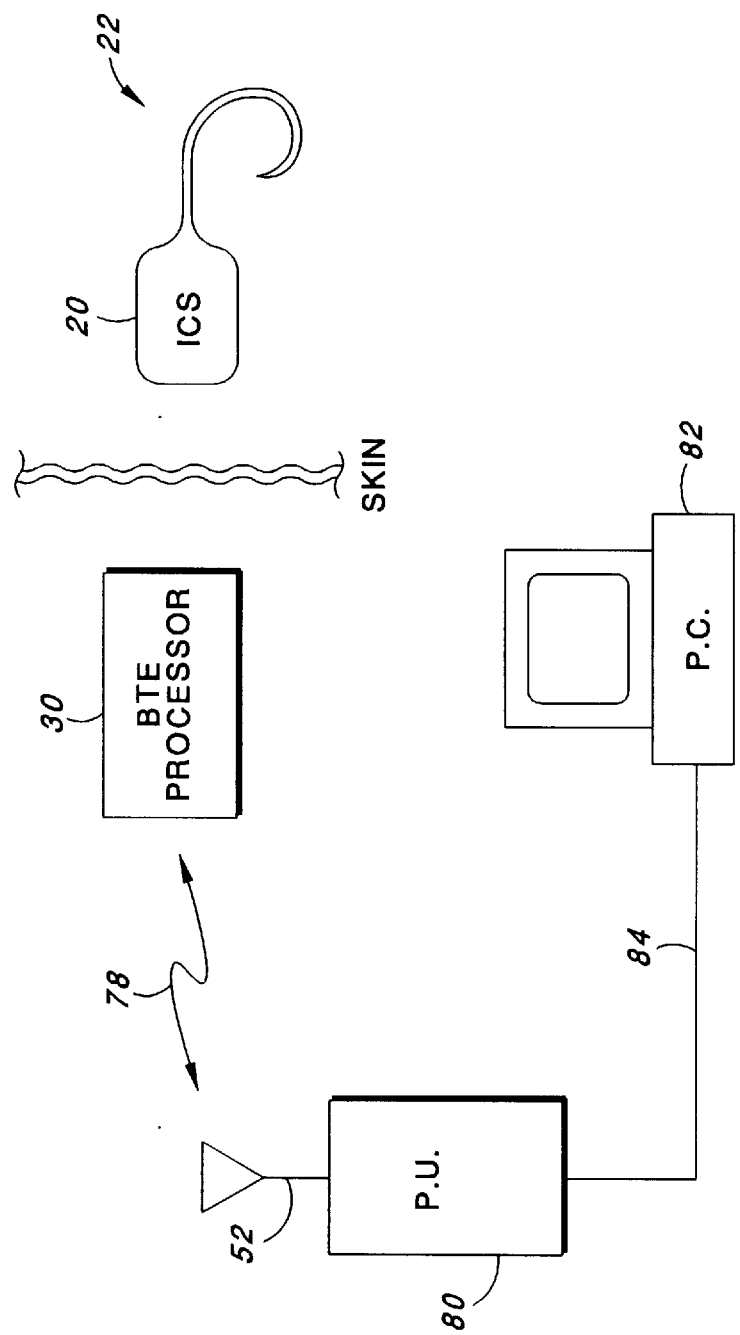
FIG. 6 is a block diagram that illustrates the use of a programming unit (PU) coupled to a personal computer (PC) for the purpose of programming and testing a BTE processor/headpiece and an ICS in accordance with the invention.

When the ICS and its electrode array are first implanted in the user, there is a need to program the ICS to operate with a prescribed electrode configuration, as well as to test the electrodes of the array to confirm which electrode pairs are working and which are not. Such configuring and/or testing is typically referred to in the art as "fitting" the ICS to its user. Fitting is best accomplished by using a special programming unit (PU) 80 adapted to interface with the BTE processor 30, as shown in FIG. 6. Typically, the PU 80 will include all of the functions of the RCU 50 plus a few more. As seen in FIG. 6, the PU 80 is coupled to a personal computer (PC) 82 via a connecting cable 84. The connecting cable 84 is connected to either the parallel port or serial port of the PC 82, and allows commands and data to be sent to and from the PC 82 from the PU 80. Conventional "fitting" software, e.g., of the type disclosed in commonly-owned U.S. patent application Ser. No. 08/456,141, Filed May 31, 1995, incorporated herein by reference, or similar or equivalent software, may then be loaded in the PC 82 to facilitate the fitting operation. The PU 80, in turn, allows all of the commands and data associated with the fitting operation to be sent to, and received from, the BTE processor 30 over an FM or other wireless link 78.

For purposes of the "fitting" function carried out by the PU 80 and PC 82, note that the FM link 78 may be bidirectional, even though in a preferred embodiment, the FM link 78 may only be unidirectional (sending signals from a transmitter in the RCU 50 to a receiver in the BTE processor 30). If bidirectionality is desired, the BTE processor 30 and PU 80 each must include both an FM transmitter and an FM receiver. The BTE processor 30, if of the type disclosed in the above-referenced ICS patent application, already includes the capability for bidirectional telemetry between the ICS 20 and the BTE processor 30.

Figure 5:
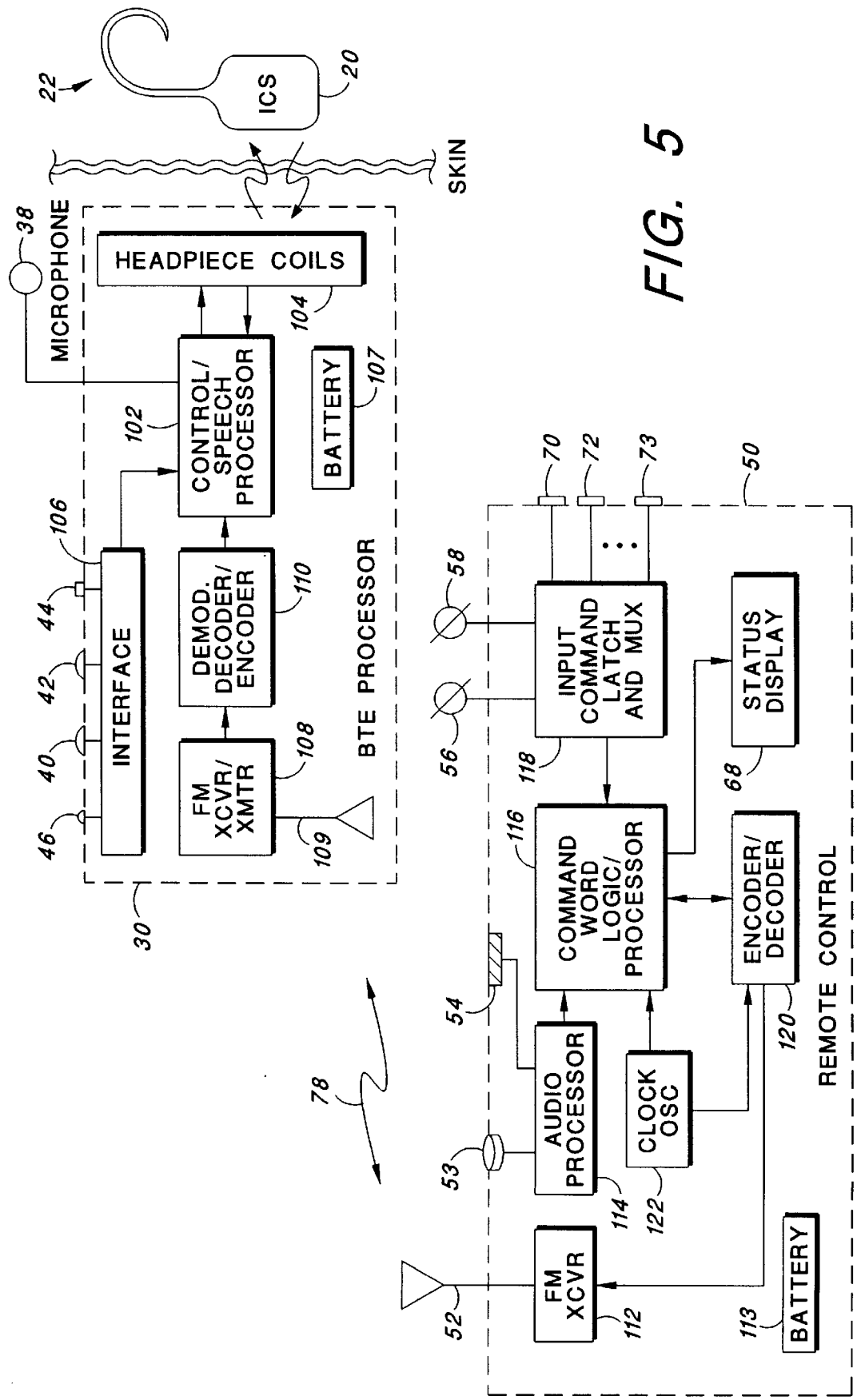
FIG. 5 is an electrical block diagram of the cochlear stimulation system of the present invention.

Turning next to FIG. 5, an electrical block diagram of a suitable BTE processor 30 and RCU 50 for use with the present invention are shown. It should be emphasized that the configuration shown in FIG. 5 does not represent all possible configurations for such circuitry. Rather, that which is shown in FIG. 5 is only representative of one configuration that could be employed to carry out the invention. Numerous variations and alternatives to that which is shown could be implemented. For example, in its simplest form, the present invention could be practiced without backtelemetry from the ICS, and corresponding backtelemetry to the RCU.

In such instance, the FM transceiver (XCVR) shown in FIG. 5, which carries out the function of both an FM transmitter and an FM receiver, could be replaced by simply an FM transmitter. Similarly, in such instance the FM receiver/transmitter (RCVR/XMTR) shown as part of the BTE processor 30 in FIG. 5 could be replaced by simply an FM receiver. Further, as has been indicated, the invention need not necessarily be limited to an FM link between the RCU and BTE processor. Rather, any kind of wireless telecommunicative link over which information may be sent, whether RF-based, e.g., with FM, AM, or other modulation, infra-red, sonic, optical, etc., could be employed, in which case appropriate transmitters and receivers associated with the type of link used would also necessarily be employed.

As seen in FIG. 5, the BTE processor 30 includes a control/speech processor 102 coupled to appropriate headpiece coils 104. The processor 102 and coils 104 correspond generally to the wearable processor 12 (WP) and headpiece assembly 14 of the prior art. (See FIG. 1.) If proper implantation of the ICS 20 is performed, i.e., so that the ICS is implanted at a location that is adequately aligned with the BTE processor 30 when the BTE processor is worn behind the ear, then the magnets that have heretofore been required in the headpiece assembly for aligning the external coils with the implanted coils of the ICS may be eliminated. However, it is to be emphasized that the present invention may be used with a BTE processor 30 regardless of whether a magnet is used within such processor 30 to achieve alignment with the ICS 20.

The BTE processor 30 includes appropriate interface circuitry 106 for interfacing with the volume adjustment knob 40, sensitivity adjustment knob 42, ON/OFF button 44, and LED 46, with the control/processor circuit 102. The BTE processor 30 further includes an FM receiver/transmitter 108, an appropriate antenna 109, and demodulation/decoding/encoding circuitry 110. The FM receiver portion of the FM receiver/transmitter circuit 108 receives the incoming FM signals over an FM link through the antenna 109. Such signals are then demodulated and decoded, as required, by the circuitry 110, and then passed to the control/processor 102, which acts on such signals to control the processor 102, or to convert the signals to appropriate command or stimulation signals that are inductively coupled into the ICS 20. A suitable FM receiver for performing the receiving function may be realized, e.g., using an "in the ear" communications receiver marketed by PHONAK Communications AG of Switzerland. Alternatively, a custom FM receiver may be designed and fabricated for carrying out this function by those of skill in the art. When the FM link uses bidirectional telemetry, any signals, e.g., status signals, generated within the BTE processor 30, or received from the ICS 20 through the headpiece coils 104, may be appropriately encoded by the circuitry 110 and then transmitted via the antenna 109 (or via a second transmitting antenna, not shown) to the RCU 50 by the FM transmitter portion of the FM RCVR/XMTR 108.

The RCU 50 sends FM signals (and may receive FM signals in some embodiments) via the antenna 52. Such signals are sent or received by an FM transceiver circuit 112 located within the RCU 50. The RCU 50 generates the command signals it sends based on control inputs from the volume or sensitivity knobs 56 or 58, or programming buttons 70, 72, 73 (which may be used to program, e.g., the threshold levels used by the fade-in and fade-out features of the invention, or other programmable parameters associated with operation of the invention); or audio input signals received via the built-in microphone 54 or the audio input jack 53 (which may be connected to any audio source device, such as a radio, CD-player, tape-player, or an external microphone). The RCU displays its operating status (e.g., current volume and sensitivity settings, battery condition, operating mode, etc.) on the status display panel 68. (When a bidirectional FM telemetry link is employed, the display panel 68 may also display signals relating to the status of the BTE processor 30 and/or ICS 20.) The status display panel may be as simple as a multicolored LED, or as sophisticated as an LCD display panel of the type commonly used in pocket pagers or notebook computers.

The LED 46 is activated, or lights up, whenever there is an appropriate signal coupled between the ICS 20 and the headpiece coils 104. Such signal, in turn, may be activated upon command from the RCU. Hence, it is possible to verify a proper coupling link between the ICS 20 and the coils 104, as well as a proper FM link between the RCU and the BTE processor 30, by sending such signal (which may be generated in response to pushing a BTE LED activate button on the RCU) from the RCU 50 to the BTE processor 30, and observing whether the LED 46 is turned ON.

All audio signals received by the RCU 50, whether from the built-in microphone 54, or from an external audio source through the audio input jack 53, are preliminarily processed by an audio processor 114. Such audio processor 114 will typically include an attenuator, or attenuation adjustment, for the signals received via the audio input jack 53. After suitable processing (e.g., amplification and filtering) such audio input signals are sent to a command word logic/processor 116. Typically, whenever an audio input plug from an external audio source (such as a tape-player, a radio, a TV, or the like) is plugged into the audio input jack 53, the built-in microphone 54 is turned off (e.g., disconnected from the audio processor 114). In this manner, audio signals are received from only one audio source at the RCU at any given time.

All command signals received from the volume or sensitivity knobs 56, 58, or the programming buttons 70, 72, 73, are latched into appropriate input command latch/multiplexing circuitry 118, and then sent to the command word logic processor 116. In the processor 116, all signals received, whether audio input signals, or command signals, are processed for transmission to the BTE processor 30. Typically, such command/audio information is formatted into frames of data, with each frame of data containing a prescribed number of data words, with each data word containing either command information or audio information depending upon its location within the data frame. A synchronizing clock signal, generated by a suitable clock oscillator circuit 122, helps control the processor 116 as it forms the frames of data. All of the words in the data frame are then sent serially through an appropriate encoder/decoder 120 to the FM XCVR 112, where they modulate an FM carrier signal, and are sent through the antenna 52 to the BTE processor 30.

One feature of the present invention relates to the manner in which the control/speech processor 102 (FIG. 5) within the BTE processor 30 responds to the informational signals received over the wireless link 78 and/or audio signals received from the BTE microphone 38. Audio signals sensed by the two microphones used with the system—a first microphone 38 being in or near the BTE processor 30, and a second microphone 54 being part of or coupled to the RCU (or other audio source plugged into the audio input port 53 in lieu of the second microphone 54)—are appropriately combined before being coupled into the ICS. Such signal combining is accomplished via appropriate processing controls (e.g., software and/or firmware) used within (or coupled to) the control/speech processor 102. For example, when the second microphone 54 at the RCU 50 is turned ON, or when another audio source (e.g., tape player) is connected to the audio input port 53 of the RCU 50, the level of the signal from the first microphone 38 at the BTE processor 30 is significantly reduced or masked. As a result, the audio signal received from the RCU 30 over the FM (or other wireless) link 78 predominates what the ICS user "hears". However, as soon as the signal received from the RCU 50 over the FM link 78 fades away, i.e., when the audio source at the remote site ceases to provide an audio signal input, then the signal level from the BTE microphone 38 returns to a normal level, thereby causing audio sounds sensed by the BTE microphone 38 to predominate what the ICS user "hears". These adjustments between the BTE microphone 38 and the RCU microphone 54 (or other audio source plugged into the audio jack 53) are performed dynamically so that the appropriate audio signals heard by the ICS user fade in and fade out as a function of whether a specified one of the signals exceeds a prescribed level. Thus, for example, so long as a signal coming by way of the RCU microphone is above a certain level, it masks out any signal from the BTE microphone. But, as soon as the RCU microphone signal drops below that certain level, then the BTE microphone signal is no longer masked out. In this way, the invention provides automatic fade-in/fade-out of a local or remote audio source. Should such fade-in and fade-out be inappropriate for a given application, then an appropriate command may be generated from the RCU 50 that turns the BTE microphone 38 completely OFF and the RCU microphone 54 ON all the time. Or, the BTE microphone 38 may be turned ON all the time and the RCU microphone 54 OFF all the time, so that audio signals from only one audio-pickup point are received by the ICS.

Both the RCU 50 and the BTE 30 are powered using replaceable batteries. The battery for the BTE processor is a small disc-shaped battery 107 (FIG. 5) of the type commonly used in hearing aids and wrist watches. The battery for the RCU 50 may be a conventional AA or AAA battery or batteries 113.

There are at least the following operating modes provided by the cochlear stimulation system of the present invention:

1. BTE Stand Alone Mode. In this mode, the user wears the BTE processor 30 and does not carry the RCU 50 with him or her. This is a limited mode wherein the BTE processor 30 may be turned on and off to the last program set previously by the RCU. The volume and/or sensitivity may also be controlled using the potentiometers 40 and 42, as required.

2. RCU Control Mode. This is the most common mode for most users of the cochlear stimulation system. In this mode, the RCU microphone 54 is deactivated. The FM transceiver 112 is idle as long as no command button 70, 72, 73 is pushed. Every command transmitted as a result of the user pushing a command button is prefixed or otherwise tagged with a BTE Identification (ID) code or word to prevent cross-talk in the event that more than one user is in the vicinity. When the RCU 50 is in this mode, it can also turn on the LED 46 mounted on the BTE processor 30, providing a positive indication of the functionality of the cochlear stimulation system. This allows, e.g., a parent or a teacher to make sure that the system is functional without disturbing the user's activity.

3. RCU Auxiliary Input Mode. In this mode, the RCU 50 may be connected to a walkman, TV, or any other auditory device through the audio input port 53 on the RCU. The RCU thus offers a wireless connection that may be desirable in many situations, e.g., sitting away from a TV set, driving a car while listening to a CD player, and many other situations. This mode is particularly advantageous when the alternative is connecting a wire from the BTE processor 50 rather than a body-worn speech processor. (Most users would prefer not to have a wire dangling from behind their ear.) Another advantage of this mode is that it guarantees a safe and smooth transition from the headpiece microphone 38 to the auxiliary input 53. Like all other FM input modes, the fade-in fade-out facility is applied so that as long as the level of input signal received from the FM transmitter (RCU 30) is above a certain level, it masks the input from the headpiece microphone 38.

4. RCU FM Transmitter Mode. In this mode, the RCU 50 is handed to another speaker who uses it as an FM transmitter. When the BTE 30 is in this mode, it is listening to the strongest signal received. In this mode, the setting of the BTE 30 cannot be changed, except for the volume (and in some models the sensitivity) which can be controlled with the volume potentiometer 40 (or the sensitivity potentiometer 42). Switching the RCU back to the RCU Control Mode sends a specific sound signal detected by the BTE processor 30 and places the BTE processor back in the control mode (wherein RCU microphone is deactivated, and the transceiver is idle until a new command is issued).

5. RCU FM Transmitter Mode with RCU Microphone Inactive. This mode is useful for appropriate situations, such as a classroom setting, where there are a number of ICS users who listen to the same speaker over the same FM channel. In this situation, one of the users gives his or her RCU in the FM mode to the speaker(s), while the others switch their RCU's to this mode—i.e., the RCU microphone 54 is disabled or turned off. This mode thus allows each user to listen to the same speaker over the same FM channel without competing signals from their own RCU. In this mode, each BTE processor 30 may first need to be programmed to recognize the prefix ID code from the particular RCU that is to be used as the common RCU.

As described above, it is thus seen that the present invention provides a cochlear stimulation system that does away with the need for an external headpiece separate and apart from an externally-worn speech processor. Such arrangement advantageously eliminates the cable that has previously been required to connect the headpiece with an external speech processor. Further, it is seen that the external speech processor and headpiece comprise one integral unit that may be worn comfortably and unobtrusively behind the ear, and wherein needed control of such behind-the-ear (BTE) processor is provided by a remote control unit (RCU) carried by the user which is telecommunicatively coupled—e.g., through an FM link—to the BTE processor.

While the invention herein disclosed has been described by means of specific embodiments and applications thereof, numerous modifications and variations could be made thereto by those skilled in the art without departing from the scope of the invention set forth in the claims.

What is claimed is:

1. A cochlear stimulation system comprising:
    an implantable cochlear stimulator (ICS), including an array of implantable electrodes for insertion into the cochlea, comprising means for stimulating selected pairs of the implantable electrodes with an electrical current of a prescribed intensity, and means for receiving an information signal, the information signal specifying which of the implantable electrodes are to receive the electrical current and the intensity of such current;

a behind-the-ear (BTE) processor comprising means for generating the information signal as a function of received command signals and audio signals, means for sending the information signal to the ICS, a plurality of manual controls for defining at least some of the received command signals, a first microphone that detects audio sounds and converts them to audio signals, and receiver means for receiving external data signals from a source remote from the BTE processor; and a remote control unit (RCU) comprising a second microphone, a plurality of command controls that when activated generate command data, means for generating data signals as a function of input signals received by the RCU, and means for transmitting the data signals to the BTE processor, the input signals received by the RCU comprising audio signals from the second microphone, audio signals derived from an electronic device, or command data generated by the command controls;

wherein the BTE processor further includes means for combining audio signals from the first microphone and audio signals from the RCU in a prescribed manner before generating the information signal and sending it to the ICS.

2. The cochlear stimulation system of claim 1 wherein the BTE processor includes an FM receiver, and wherein the means for transmitting the data signals to the BTE processor from the RCU comprises an FM transmitter.

3. The cochlear stimulation system of claim 2 wherein the prescribed manner in which the audio signals from the first microphone and audio signals from the RCU are combined comprises means for reducing the magnitude of the audio signal from the first microphone below the magnitude of the audio signal received from the RCU whenever the audio signal received from the RCU exceeds a first threshold.

4. The cochlear stimulation system of claim 2 wherein the prescribed manner in which the audio signals form the first microphone and audio signals from the RCU are combined comprises means for reducing the magnitude of the audio signal from the RCU below the magnitude of the audio signal received from the first microphone whenever the audio signal received from the RCU is less than a second threshold.

5. The cochlear stimulation system of claim 1 wherein the electronic device from which the RCU may receive audio signals comprises a radio, a tape player, a CD player, a television, a telephone, or a personal computer.

6. The cochlear stimulation system of claim 1 wherein the RCU includes display means for displaying information related to the status of the command controls, command data or data signals.

7. The cochlear stimulation system of claim 1 wherein the BTE processor further includes visual indicating means for visually indicating whether a link over which the information signal may be sent has been established between the ICS and BTE.

8. The cochlear stimulation system of claim 7 wherein the command controls of said RCU include means for enabling/disabling said visual indicating means of said BTE.

9. The cochlear stimulation system of claim 1 wherein the RCU includes means for selectively tagging the data signal sent to the BTE processor with a unique identification (ID) signal, and wherein the BTE processor includes means for responding to the data signal received from the RCU only when said ID signal is present, whereby the BTE processor only responds to data signals from the RCU that have been tagged with the unique ID signal.

10. A cochlear stimulation system comprising:

an implantable cochlear stimulator (ICS), including an array of implantable electrodes for insertion into the cochlea, comprising means for stimulating selected pairs of the implantable electrodes with an electrical current of a prescribed intensity, and means for receiving an information signal, the information signal specifying which of the implantable electrodes are to receive the electrical current and the intensity of such current; and a behind-the-ear (BTE) processor comprising means for generating the information signal as a function of command signals and audio signals, means for sending the information signal to the ICS, means for confirming that a link has been established between the BTE processor and the ICS through which the information signal may be sent, a plurality of manual controls for defining the command signals, a microphone that detects audio sounds and converts them to audio signals, and a replaceable battery that provides operating power for said BTE processor.

11. The cochlear stimulation system of claim 10 wherein the confirmation means comprises a light-emitting diode (LED) that is turned ON whenever the link is established between the ICS and the BTE.

12. The cochlear stimulation system of claim 10 wherein the plurality of manual controls included on the BTE include a volume control and an ON/OFF switch.

13. The cochlear stimulation system of claim 12 wherein the plurality of manual controls included on the BTE further includes a sensitivity control.

14. The cochlear stimulation system of claim 10 further including means for mounting the microphone inside of the BTE.

15. The cochlear stimulation system of claim 10 wherein the BTE includes a microphone tube secured to the BTE that, when the BTE is worn on an ear of a user, enters the ear canal of said user, and wherein the microphone is mounted on said microphone tube inside of said ear canal.

16. The cochlear stimulation system of claim 10 further including control means other than said plurality of manual controls for selectively controlling the operation of said BTE processor.

17. The cochlear stimulation system of claim 16 wherein said control means comprises a remote control unit (RCU) comprising a second microphone, a plurality of command controls that when activated generate command data, means for generating data signals as a function of input signals received by the RCU, and means for transmitting the data signals to the BTE processor, the input signals received by the RCU comprising audio signals from the second microphone, audio signals derived from an electronic device, or command data generated by the command controls.

18. A cochlear stimulation system comprising:

an implantable cochlear stimulator (ICS), including an array of implantable electrodes for insertion into the cochlea, comprising means for stimulating selected pairs of the implantable electrodes with an electrical current of a prescribed intensity, and means for receiving an information signal, the information signal specifying which of the implantable electrodes are to receive the electrical current and the intensity of such current;

a behind-the-ear (BTE) processor comprising means for generating the information signal as a function of received command signals and audio signals, means for sending the information signal to the ICS, visual indicating means for visually indicating whether a link over which the information signal may be sent has been established between the ICS and BTE, a plurality of manual controls for defining at least some of the received command signals, a first microphone that detects audio sounds and converts them to audio signals, and receiver means for receiving external data signals from a source remote from the BTE processor; and a remote control unit (RCU) comprising a second microphone, a plurality of command controls that when activated generate command data, means for generating data signals as a function of input signals received by the RCU, and means for transmitting the data signals to the BTE processor, the input signals received by the RCU comprising audio signals from the second microphone, audio signals derived from an electronic device, or command data generated by the command controls.

19. The cochlear stimulation system of claim 18 wherein the command controls of said RCU include means for enabling/disabling said visual indicating means of said BTE.

20. A cochlear stimulation system comprising:

an implantable cochlear stimulator (ICS), including an array of implantable electrodes for insertion into the cochlea, comprising means for stimulating selected pairs of the implantable electrodes with an electrical current of a prescribed intensity, and means for receiving an information signal, the information signal specifying which of the implantable electrodes are to receive the electrical current and the intensity of such current;

a behind-the-ear (BTE) processor comprising means for generating the information signal as a function of received command signals and audio signals, means for sending the information signal to the ICS, a plurality of manual controls for defining at least some of the received command signals, a first microphone that detects audio sounds and converts them to audio signals, and receiver means for receiving eternal data signals from a source remote from the BTE processor; and a remote control unit (RCU) comprising a second microphone, a plurality of command controls that when activated generate command data, means for generating data signals as a function of input signals received by the RCU, and means for transmitting the data signals to the BTE processor, the input signals received by the RCU comprising audio signals from the second microphone, audio signals derived from an electronic device, or command data generated by the command controls; and wherein the RCU includes means for selectively tagging the data signal sent to the BTE processor with a unique identification (ID) signal, and wherein the BTE processor includes means for responding to the data signal received from the RCU only when said ID signal is present, whereby the BTE processor only responds to data signals from the RCU that have been tagged with the unique ID signal.

21. A cochlear stimulation system comprising:

an implantable cochlear stimulator (ICS), including an array of implantable electrodes for insertion into the cochlea, comprising means for stimulating selected pairs of the implantable electrodes with an electrical current of a prescribed intensity, and means for receiving an information signal, the information signal specifying which of the implantable electrodes are to receive the electrical current and the intensity of such current; and a behind-the-ear (BTE) processor comprising means for generating the information signal as a function of command signals and audio signals, means for sending the information signal to the ICS, a plurality of manual controls for defining the command signals; a microphone tube secured to the BTE that, when the BTE is worn on an ear of a user, enters the ear canal of said user; a microphone mounted on the end of the microphone tube that is inside of the ear canal when the BTE is worn that detects audio sounds and converts them to audio signals, and a replaceable battery that provides operating power for said BTE processor.

* * * * *